(12) United States Patent
Minamihata

(10) Patent No.: US 10,416,145 B2
(45) Date of Patent: Sep. 17, 2019

(54) METHOD FOR EVALUATING ABRASIVE GRAINS, AND METHOD FOR MANUFACTURING SILICON WAFER

(71) Applicant: SUMCO CORPORATION, Tokyo (JP)

(72) Inventor: Yuuji Minamihata, Tokyo (JP)

(73) Assignee: SUMCO CORPORATION, Tokyo (JP)

( * ) Notice: Subject to any disclaimer, the term of this patent is extended or adjusted under 35 U.S.C. 154(b) by 156 days.

(21) Appl. No.: 15/535,567

(22) PCT Filed: Oct. 9, 2015

(86) PCT No.: PCT/JP2015/078852
§ 371 (c)(1),
(2) Date: Jun. 13, 2017

(87) PCT Pub. No.: WO2016/103854
PCT Pub. Date: Jun. 30, 2016

(65) Prior Publication Data
US 2017/0343528 A1    Nov. 30, 2017

(30) Foreign Application Priority Data

Dec. 26, 2014  (JP) ................................. 2014-265757

(51) Int. Cl.
*G01N 33/40* (2006.01)
*G01N 21/49* (2006.01)
(Continued)

(52) U.S. Cl.
CPC ............. *G01N 33/40* (2013.01); *B24B 27/06* (2013.01); *B24B 57/02* (2013.01); *B28D 5/007* (2013.01);
(Continued)

(58) Field of Classification Search
CPC ............... G01N 33/40; G01N 15/0631; G01N 2015/0675; G01N 2021/1738;
(Continued)

(56) References Cited

U.S. PATENT DOCUMENTS

| 4,291,980 | A | * | 9/1981 | Patterson | ............. | G01N 21/278 |
|---|---|---|---|---|---|---|
| | | | | | | 73/61.41 |
| 6,006,738 | A | * | 12/1999 | Itoh | ........................ | B28D 5/007 |
| | | | | | | 125/16.01 |

(Continued)

FOREIGN PATENT DOCUMENTS

| CN | 1502666 A | 6/2004 |
|---|---|---|
| CN | 101891194 | 11/2010 |

(Continued)

OTHER PUBLICATIONS

Office Action issued in Chinese family member Patent Appl. No. 201580068516.2, dated Jun. 27, 2018, along with an English translation thereof.

(Continued)

*Primary Examiner* — Harshad R Patel
*Assistant Examiner* — Tran M. Tran
(74) *Attorney, Agent, or Firm* — Greenblum & Bernstein, P.L.C.

(57) ABSTRACT

An evaluation method of abrasive grains used in an ingot-cutting slurry includes: an evaluation solution preparation step in which abrasive grains including polishing grains and impurities are dissolved in a solvent to prepare an evaluation solution; a sedimentation step in which a container containing the evaluation solution is left still to settle the polishing grains; a measurement step in which a turbidity of supernatant of the evaluation solution is measured using the measurement device; and an estimation step in which an (Continued)

amount of the impurities is estimated based on the measurement result of the turbidity of the supernatant.

5 Claims, 13 Drawing Sheets

(51) Int. Cl.
| | |
|---|---|
| B24B 27/06 | (2006.01) |
| B24B 57/02 | (2006.01) |
| H01L 21/304 | (2006.01) |
| G01N 21/51 | (2006.01) |
| C09K 3/14 | (2006.01) |
| G01N 15/06 | (2006.01) |
| B28D 5/00 | (2006.01) |
| G01N 15/00 | (2006.01) |
| G01N 21/94 | (2006.01) |
| G01N 21/85 | (2006.01) |

(52) U.S. Cl.
CPC ............ *C09K 3/14* (2013.01); *G01N 15/06* (2013.01); *G01N 21/49* (2013.01); *G01N 21/51* (2013.01); *H01L 21/304* (2013.01); *G01N 21/85* (2013.01); *G01N 21/94* (2013.01); *G01N 2015/0053* (2013.01); *Y02P 70/179* (2015.11)

(58) Field of Classification Search
CPC ..... G01N 2021/174; G01N 2021/1742; G01N 2021/1744; G01M 2015/0053; C09G 1/02; C09K 3/1463
See application file for complete search history.

(56) References Cited

U.S. PATENT DOCUMENTS

| | | | | |
|---|---|---|---|---|
| 6,161,533 A * | 12/2000 | Katsumata | ............. | B28D 5/007 125/16.01 |
| 6,482,325 B1 * | 11/2002 | Corlett | ............... | B01D 21/0009 210/662 |
| 6,668,625 B2 * | 12/2003 | Weis | ............... | G01F 23/14 73/61.63 |
| 7,025,796 B2 | 4/2006 | Komiya et al. | | |
| 7,731,801 B2 * | 6/2010 | Takemura | ................ | B08B 3/04 134/1.3 |
| 8,685,123 B2 * | 4/2014 | Wang | ..................... | B82Y 30/00 51/307 |
| 8,696,404 B2 * | 4/2014 | Sun | ......................... | B24B 57/02 210/195.1 |
| 8,696,929 B2 * | 4/2014 | Kurata | ................ | B24B 37/0056 252/79.1 |
| 9,039,796 B2 * | 5/2015 | Iwano | ..................... | C09G 1/02 51/293 |
| 9,192,941 B2 * | 11/2015 | Presby | ..................... | B07B 1/18 |
| 9,796,894 B2 * | 10/2017 | Takahashi | ............... | B24B 57/02 |
| 9,881,801 B2 * | 1/2018 | Iwano | ..................... | C09G 1/02 |
| 9,970,869 B2 * | 5/2018 | Schwerdtfeger | ..... | G01N 21/532 |
| 2006/0075687 A1 * | 4/2006 | Tsuruta | ................ | B28D 5/007 51/307 |
| 2015/0098887 A1 | 4/2015 | Iwano et al. | | |

FOREIGN PATENT DOCUMENTS

| | | |
|---|---|---|
| JP | 10-52816 | 2/1998 |
| JP | 2004-111416 | 4/2004 |
| JP | 2004-219391 A | 8/2004 |
| WO | 2013/175859 | 11/2013 |
| WO | 2015/091495 | 6/2015 |

OTHER PUBLICATIONS

International Search Report, along with English-language translation thereof, issued in PCT/JP2015/078852, dated Dec. 8, 2015.
Written Opinion of the International Searching Authority, along with English-language translation thereof, issued in PCT/JP2015/078852, dated Dec. 8, 2015.
International Preliminary Report on Patentability issued in PCT/JP2015/078852, dated Jun. 27, 2017.
Office Action, along with an english translation thereof, issued in Taiwan Counterpart Patent Appl. No. 104132353, dated Nov. 3, 2016.
Office Action issued in Japanese family member Patent Appl. No. 201580068516.2, dated Jun. 27, 2018 , along with an English translation thereof.

* cited by examiner

METHOD FOR EVALUATING ABRASIVE GRAINS, AND METHOD FOR MANUFACTURING SILICON WAFER

TECHNICAL FIELD

The present invention relates to an evaluation hod of abrasive grains and a manufacturing method of a silicon wafer.

BACKGROUND ART

Methods for manufacturing silicon wafers from a silicon monocrystal ingot have been known (see, for instance, Patent Literature 1).

According to the method disclosed in Patent Literature 1, a silicon ingot is pressed against a wire in motion while slurry containing polishing grains having a mean particle diameter ranging from 13 μm to 15 μm is supplied to the wire, thereby cutting the silicon ingot and manufacturing silicon wafers.

CITATION LIST

Patent Literature(s)

Patent Literature 1 JP-10-52816 A

SUMMARY OF THE INVENTION

Problem(s) to be Solved by the Invention

However, the polishing grains used in the method disclosed in Patent Literature 1 contain impurities such as FC (Free Carbon) having a diameter of 3 μm or less not contributing to enhancement in cutting performance, as well as polishing grains such as GC (Green silicon Carbide) capable of enhancing cutting performance. When an ingot is cut using slurry containing the polishing grains as mentioned above, the impurities present between the polishing grains and the ingot may deteriorate the cutting performance of the wire saw to lower the quality of the silicon wafer. Since the occurrence of such a phenomenon cannot be recognized until the cutting of the ingot is finished, a method allowing an appropriate judgment whether or not a high-quality silicon wafer can be obtained prior to cutting an ingot has been desired.

An object of the invention is to provide an evaluation method of abrasive grains and a manufacturing method of a silicon wafer that enable a judgment on whether or not a high-quality silicon wafer can be obtained prior to cutting the ingot.

Means for Solving the Problem(s)

An evaluation method of abrasive grains according to an aspect of the invention is usable for an ingot-cutting slurry, the evaluation method including: preparing an evaluation solution by dissolving abrasive grains including polishing grains and impurities in a solvent; settling the polishing grains by leaving still a container containing the evaluation solution; measuring a turbidity of a supernatant of the evaluation solution using a measurement device; and estimating an amount of the impurities based on measurement results of the turbidity of the supernatant.

The abrasive grains used in the ingot-cutting slurry sometimes contain impurities in a form of the FC and the like as well as polishing grains in a form of the GC. In this case, since the relative density of the polishing grains is larger than the relative density of the impurities and there is no large difference between the sizes of the polishing grains and the impurities, the sedimentation speed of the polishing grains in the evaluation solution becomes faster than the sedimentation speed of the impurities.

According to the above aspect of the invention, the polishing grains are settled while the impurities are left present in the supernatant in the sedimentation step, and the turbidity of the supernatant is measured using the measurement device. Accordingly, the impurities can be kept from being mixed up with the polishing grains during the measurement, and the amount of the impurities estimated based on the turbidity measurement results of the supernatant can be made substantially the same as the amount of the impurities contained in the abrasive grains. Consequently, whether or not a high-quality silicon wafer can be obtained can be appropriately judged before the ingot is cut using the abrasive grains taken from the same lot as the evaluated abrasive grains.

In the evaluation method of abrasive grains according to the above aspect of the invention, it is preferable that the solvent is water, pure water or ultra-pure water.

According to the above arrangement, since water, pure water or ultra-pure water is used as the solvent, the sedimentation speed of the polishing grains in the evaluation solution can be accelerated as compared to an instance in which, for instance, an oil used for the preparation of the slurry is used as the solvent. Accordingly, the evaluation time of the abrasive grains can be reduced.

In the evaluation method of abrasive grains according to the above aspect of the invention, it is preferable that the settling is performed after shaking the container containing the evaluation solution.

According to the above arrangement, through the shaking step, the impurities adhered on the polishing grains can be separated from the polishing grains. Accordingly, the difference between the amount of impurities estimated based on the turbidity measurement results of the supernatant and the amount of impurities actually contained in the abrasive grains can be made smaller than that in an instance without performing the shaking step, thereby allowing a more appropriate judgment on whether or not a high-quality silicon wafer can be obtained.

In the evaluation method of abrasive grains according to the above aspect of the invention, it is preferable that the measuring is performed after diluting the supernatant.

When the supernatant is not diluted and there are much amount of the impurities, the turbidity sometimes exceeds a measurement range upper limit of a measurement device and the amount of the impurities may not be appropriately estimated.

In contrast, since the dilution step is performed in the above arrangement, the turbidity is restrained from exceeding the measurement range upper limit of the measurement device, thereby allowing an appropriate estimation of the amount of the impurities.

In the evaluation method of abrasive grains according to the above aspect of the invention, it is preferable that the abrasive grains used in the ingot-cutting slurry are SiC.

According to the above arrangement, the amount of the FC whose amount is especially large in the impurities can be appropriately evaluated. Accordingly, as compared to an instance in which the amount of impurities other than the FC is to be evaluated, whether or not a high-quality silicon wafer can be obtained can be more appropriately judged.

A manufacturing method of a silicon wafer according to another aspect of the invention uses a wire saw, the method including: judging whether or not the abrasive grains used in the ingot-cutting slurry is acceptable based on an estimation result obtained in the estimating in the above-described evaluation method of abrasive grains; preparing the ingot-cutting slurry using the abrasive grains that are judged to be acceptable; and cutting an ingot using the wire saw and the ingot-cutting slurry to produce the silicon wafer.

According to the above aspect of the invention, a high-quality silicon wafer can be obtained.

BRIEF DESCRIPTION OF DRAWING(S)

DESCRIPTION OF EMBODIMENT(S)

Exemplary embodiment(s) of the invention will be described below with reference to the attached drawings.
Arrangement of Wire Saw Initially, an arrangement of a wire saw will be described below.

Figure 1:
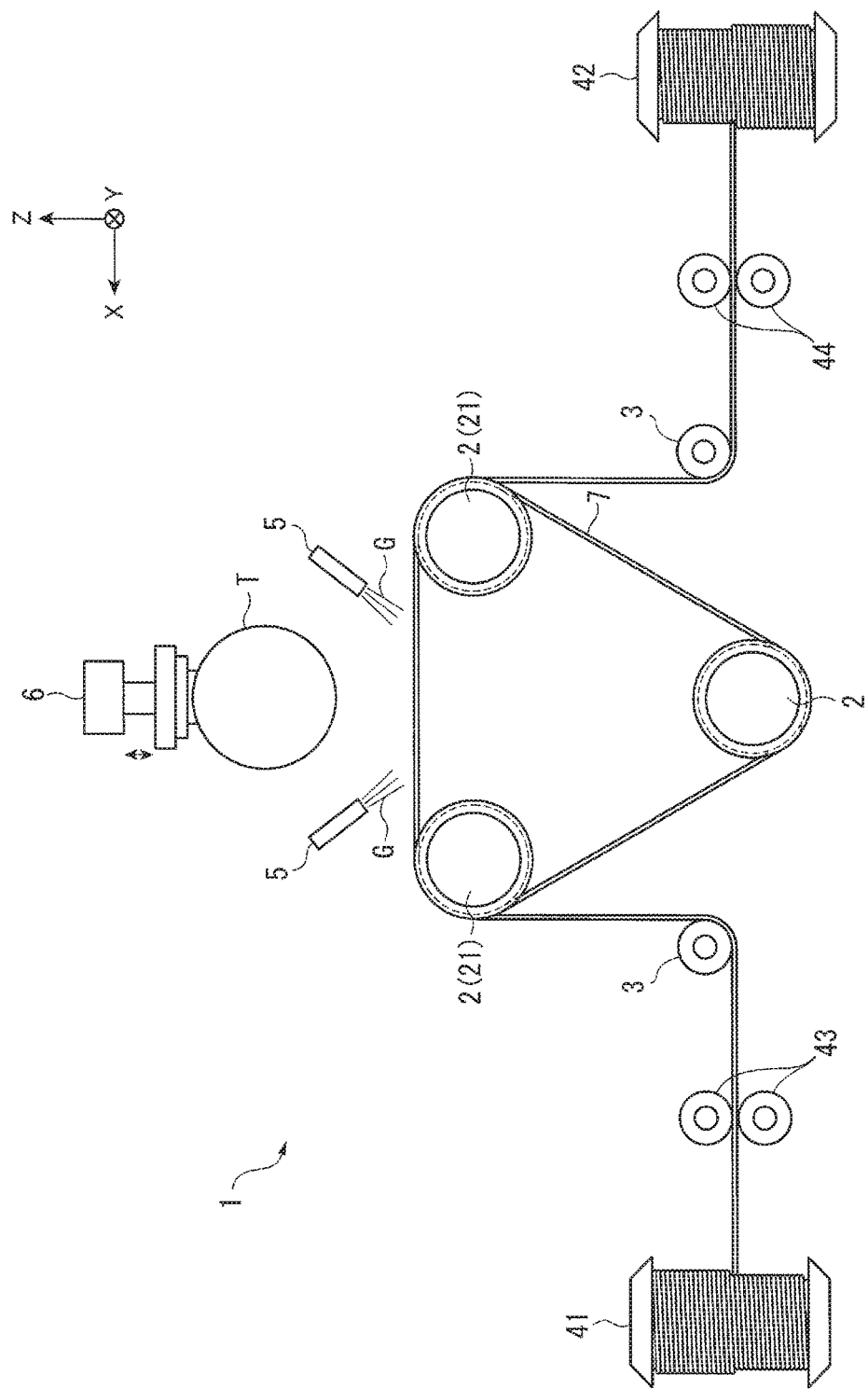
FIG. 1 is a schematic illustration of a wire saw according to an exemplary embodiment of the invention.

As shown in FIG. 1, a wire saw 1 includes three main rollers 2 including two main roller 2 on a common horizontal plane and one main roller 2 disposed between and below the two main rollers. A wire 7 is wound around the three main rollers 2 along an axial direction thereof. Wire reels 41, 42 each configured to feed and rewind the wire 7 via a plurality of guide rollers 3 (only one shown for each of the wire reels 41, 42 in FIG. 1) are respectively provided on both ends of the wire 7. Traversers 43, 44 are respectively provided between one of the guide rollers 3 and the wire reel 41 and between another one of the guide rollers 3 and the wire reel 42. The traversers 43, 44 are configured to adjust the feeding and rewinding positions of the wire 7. Nozzles 5 each configured to supply slurry G to a position between the two main rollers 2 on the upper side (referred to as upper main rollers 21 hereinafter) are provided above the two upper main rollers 21. A feeder 6 configured to hold and vertically move an ingot is provided above the nozzles 5.

The wire saw 1 is configured to rotate the plurality of main rollers 2 to drive the wire 7 in a direction substantially orthogonal to axial directions of the main rollers 2 (i.e. right-left direction), where the ingot T is lowered to be pressed against the wire 7 in motion while supplying the slurry G between the two upper main rollers 21, thereby cutting the ingot T into a plurality of silicon wafers.
Manufacturing Method of Silicon Wafer Next, a manufacturing method of the silicon wafer will be described below.

It should be noted that, in this exemplary embodiment, abrasive grains exemplarily contain polishing grains in a form of GC and impurities in a form of FC. Further, unused grains having never been used for cutting the ingot T are exemplarily used as the abrasive grains.

Figure 2:
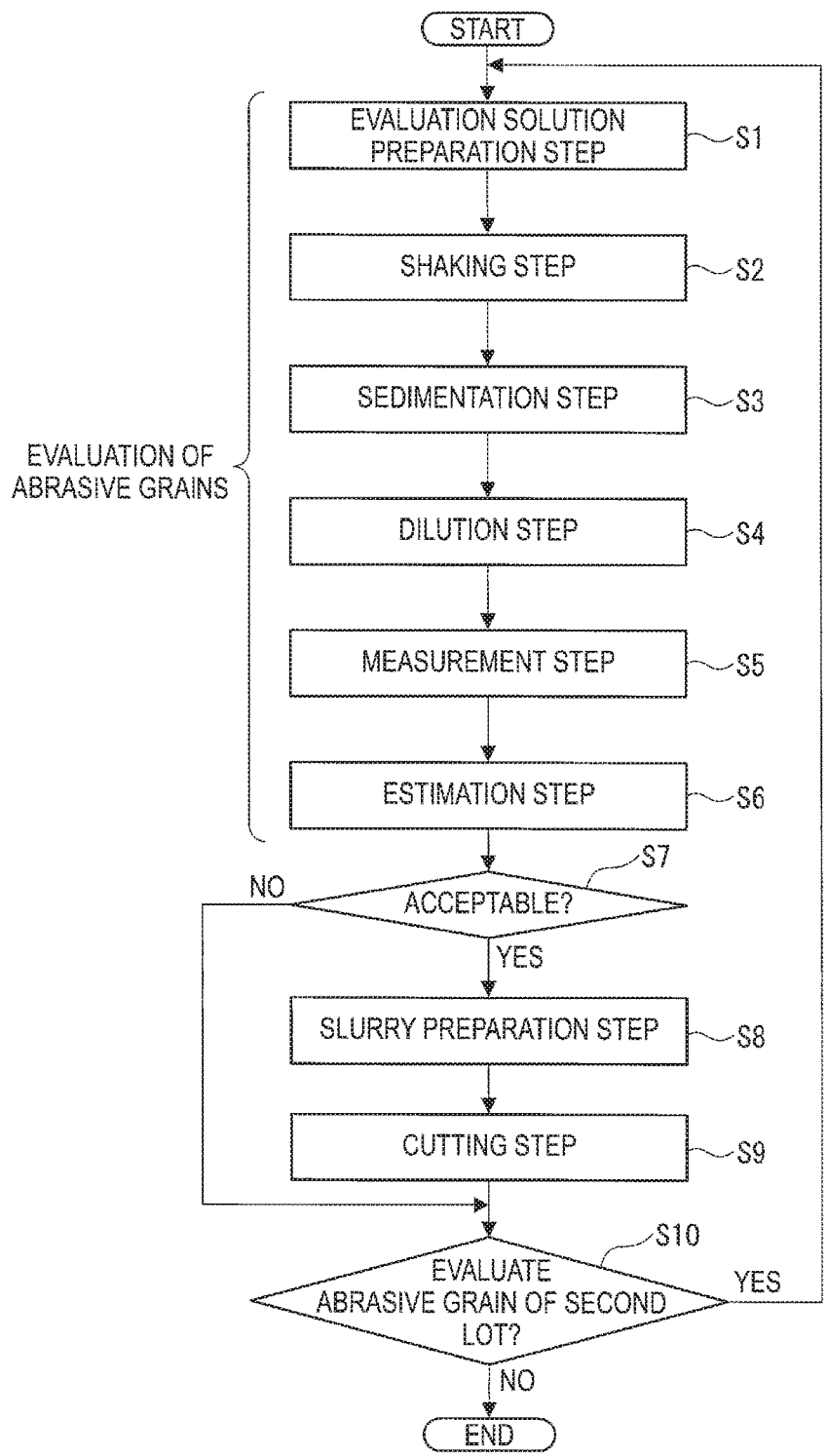
FIG. 2 is a flowchart showing a manufacturing method of a silicon wafer according to the exemplary embodiment.

Initially, as shown in FIG. 2, the abrasive grains used for the slurry G are evaluated prior to producing the slurry G. During the evaluation of the abrasive grains, an evaluation solution preparation step (Step S1), a shaking step (Step S2), a sedimentation step (Step S3), a dilution step (Step S4), a measurement step (Step S5), and an estimation step (Step S6) are performed.

In the evaluation solution preparation step (Step S1), a colorimetric tube is used as a container, in which the abrasive grains containing the GC (polishing grains) are dissolved in a solvent (pure water) to prepare an evaluation solution. The evaluation solution may be prepared through a manual operation by an operator or using a machine.

In the shaking step (Step S2), the colorimetric tube containing the evaluation solution is shaken. In the shaking step, though the colorimetric tube may be manually shaken, the colorimetric tube is preferably shaken using a machine in view of reproducibility of the shaking conditions and workload imposed on an operator. Through the shaking step, the FC adhered on the GC can be separated from the GC.

In the sedimentation step (Step S3), the colorimetric tube containing the evaluation solution is left still to settle the GC. Though the length of the time for settling the GC is not specifically limited, the time is preferably long enough for substantially all of the GC to be settled and for the FC to be present in a supernatant.

In the dilution step (Step S4), the supernatant of the evaluation solution is diluted using the solvent used in Step S1. Though the dilution ratio is not specifically limited but depending on the concentration of the FC in the evaluation solution, the dilution ratio is preferably adjusted so that the turbidity of the supernatant after the dilution does not exceed a measurement range upper limit of a measurement device (described below).

In the measurement step (Step S5), the turbidity of the supernatant of the evaluation solution is measured using the measurement device. Though any measurement device may be used, a measurement device capable of digitalizing the turbidity of the evaluation solution is suitably usable. Examples of the measurement device include a turbidity meter, which is a sort of an absorptiometer.

In the estimation step (Step S6), the amount of the FC contained in the abrasive grains is estimated based on the turbidity measurement results of the supernatant.

After performing the processes of Step S1 to S6, whether or not the abrasive grains are acceptable is judged based on the estimation results of the FC (Step S7: GO/NG judgment step).

For instance, when the measured value by the turbidity meter corresponding to the estimated amount of the FC is equal to or more than a threshold, the abrasive grains are judged not acceptable because abrasive grains taken from the same lot as the measured abrasive grains contain too much FC to obtain a high-quality silicon wafer when the ingot T is cut using the abrasive grains. On the other hand, when the measured value by the turbidity meter is less than the threshold, it is judged that the amount of the FC is small enough to obtain a high-quality silicon wafer and the abrasive grains are judged to be acceptable. It should be noted that the process in Step S7 may be performed using a machine or by an operator.

When it is judged that the abrasive grains are acceptable in Step S7, the slurry G is prepared using the abrasive grains taken from the same lot as the evaluated abrasive grains, an oil-based or water soluble oil and the like (Step S8: slurry preparation step). Subsequently, the slurry G is used to cut the ingot T (Step S9: cutting step) to produce the silicon wafer.

On the other hand, when it is judged that the abrasive grains are not acceptable in Step S7, whether or not the abrasive grains of a second lot are to be evaluated is judged (Step S10). When it is judged in Step S10 that the abrasive grains of the second lot are to be evaluated, the above process is performed for the abrasive grains from the other lot. When it is judged that the abrasive grains of the second lot are not to be evaluated, the process is terminated.

Advantage(s) of Exemplary Embodiment(s)

The following advantages can be obtained by the above-described exemplary embodiment.

(1) In the sedimentation step, the GC is settled whereas the FC remains present n the supernatant without being settled, and the turbidity of the supernatant is measured, so that the FC is kept from being mistakenly measured as the GC and the amount of the FC estimated based on the turbidity measurement results of the supernatant can be made substantially the same as the amount of the FC actually contained in the unused abrasive grains. Accordingly, whether or not a high-quality silicon wafer can be obtained can be appropriately judged before the ingot T is cut using the abrasive grains taken from the same lot as the evaluated abrasive grains.

In addition, even when the amount of the FC falls below an acceptable lower limit, the variation in the amount of the FC for each lot can be recognized. Accordingly, by reporting the variation to a manufacturer of the abrasive grains, improvement in the manufacturing conditions of the abrasive grains can be promoted.

(2) Since pure water is used as the solvent for the preparation of the evaluation solution, the sedimentation speed of the GC in the evaluation solution can be accelerated as compared to an instance in which, for instance, oil used for the preparation of the slurry G is used as the solvent, so that the evaluation time of the abrasive grains can be reduced.

(3) Since the FC adhered to the GC is separated in the shaking step, the difference between the FC amount estimated based on the turbidity measurement results of the supernatant and the FC amount actually contained in the abrasive grains can be made smaller than that in an instance without performing the shaking step, thereby allowing a more appropriate judgment on whether or not a high-quality silicon wafer can be obtained.

(4) Since the dilution step is performed depending on the concentration of the FC in the evaluation solution, the turbidity is restrained from exceeding the measurement range upper limit of the measurement device, thereby allowing an appropriate estimation of the FC amount.

Modification(s)

It should be understood that the scope of the invention is not limited by the above-described exemplary embodiment, but may encompass various improvements and modifications in designs as long as such improvements and modifications are compatible with the invention.

Specifically, the solvent used for preparing the evaluation solution may alternatively be ultra-pure water that is purer than pure water or water that is less pure than pure water. The same advantages as in the above-described exemplary embodiment can be obtained by the above arrangement.

The solvent used for preparing the evaluation solution may alternatively be an oil-based or water soluble oil as long as the polishing grains eventually settle after the sedimentation step.

When it is known that the amount of impurities adhered to the polishing grains does not exert much influence on the turbidity measurement results, the shaking step may be omitted.

When an operator can judge that the turbidity of the supernatant does not exceed the measurement range upper limit of the measurement device through a visual check after the sedimentation step, the dilution step may be omitted.

In the dilution step, a solvent other than the solvent used in Step S1 may be used for dilution. For instance, highly pure water or water may be used for dilution in the above-described exemplary embodiment.

Though the unused abrasive grains are evaluated in the above-described exemplary embodiment, recycled abrasive grains may alternatively be evaluated.

Examples

Next, the invention will be described below in more detail with reference to Examples and Comparatives. It should be noted, however, that the scope of the invention is by no means limited by the Examples and Comparatives.

Study on Dilution Step

Experiment 1

Initially, as the unused abrasive grains used for ingot-cutting slurry, abrasive grains A1, A2 manufactured by A company, abrasive grains B1, B2 manufactured by B company, abrasive grains C manufactured by C company, and abrasive grains D manufactured by D company were prepared. The production lot of the abrasive grains A1 was different from the production lot of the abrasive grains A2. Similarly, the production lot of the abrasive grains B1 was different from the production lot of the abrasive grains B2. The particle size of each of the abrasive grains was #2000.

Next, 30 gram of the abrasive grains A1 were mixed with 70 ml of pure water (solvent) through a manual operation of an operator to prepare an evaluation solution A1. Further, evaluation solutions A2, B1, B2, C, D were prepared under the same conditions as those in preparing the evaluation solution A1 except that the abrasive grains A1 were changed respectively to abrasive grains A2, B1, B2, C, D.

Figure 3:
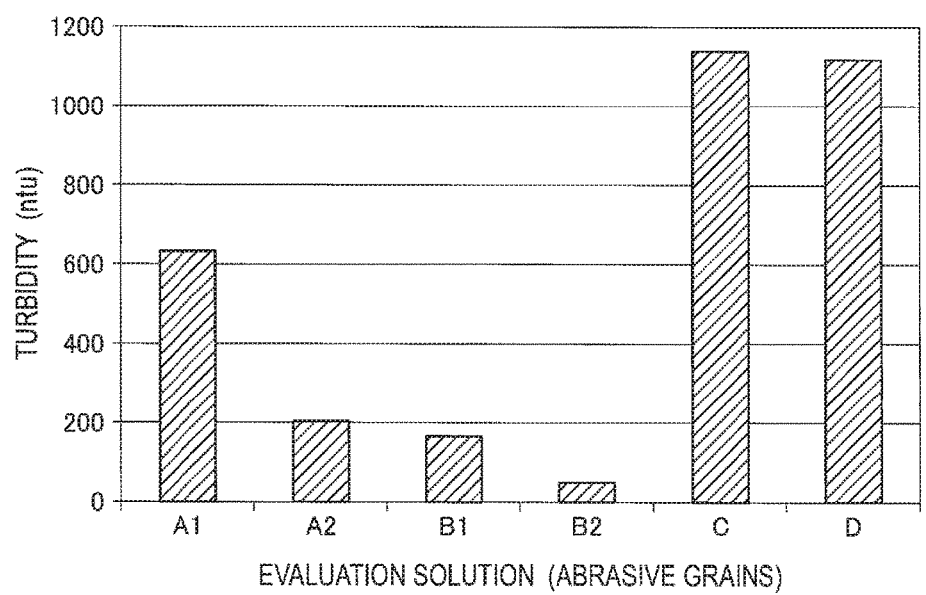
FIG. 3 is a graph showing a relationship between abrasive grains and turbidity when a stand-still time is constant in Experiment 1 in Examples of the invention.

Then, the containers (colorimetric tube) respectively containing the evaluation solutions A1, A2, B1, B2, C, D were left still for 3 hours at a normal temperature to settle the polishing grains and the turbidity of the supernatant of each of the evaluation solutions A1, A2, B1, B2, C, D was measured. The turbidity was measured using a transmission-scattering-light comparison measurement turbidity meter (manufactured by LUTRON ELECTRONIC ENTERPRISE CO., LTD, model No.: TU-2016, measurement range: 0 ntu to 1000 ntu). The results are shown in FIG. 3. It should be noted that the measurement unit is ntu (Nephelometric Turbidity Unit), where the larger ntu indicates larger turbidity.

As shown in FIG. 3, the turbidities of the evaluation solutions B1, B2 were lower than the turbidities of the other evaluation solutions.

However, when the evaluation solutions were visually checked, the turbidities of the evaluation solutions B1, B2 were noticeably larger than the turbidities of the other evaluation solutions, contrarily to the results of the measured values of turbidity. In contrast, the measured value of turbidity and the visual observation results were made substantially the same for the evaluation solutions A1, A2, C, D.

In view of the above, it is speculated that, since the evaluation solutions B1, B2 contained much amount of impurities, the turbidity of the supernatant was so large as to exceed the measurement range upper limit of the turbidity meter, and the turbidity could not be accurately measured. It is also speculated that the turbidities of the supernatants of the evaluation solutions A1, A2, C, D were within the measurement range of the turbidity meter and thus the turbidity was accurately measured.

Experiment 2

As described above, the turbidity of the supernatant of the evaluation solution sometimes cannot be appropriately measured using a turbidity meter. Accordingly, it was checked whether or not the turbidity of the supernatant became so small as to be within the measurement range of the turbidity meter by lengthening the stand-still time after preparing the evaluation solution.

Figure 4:
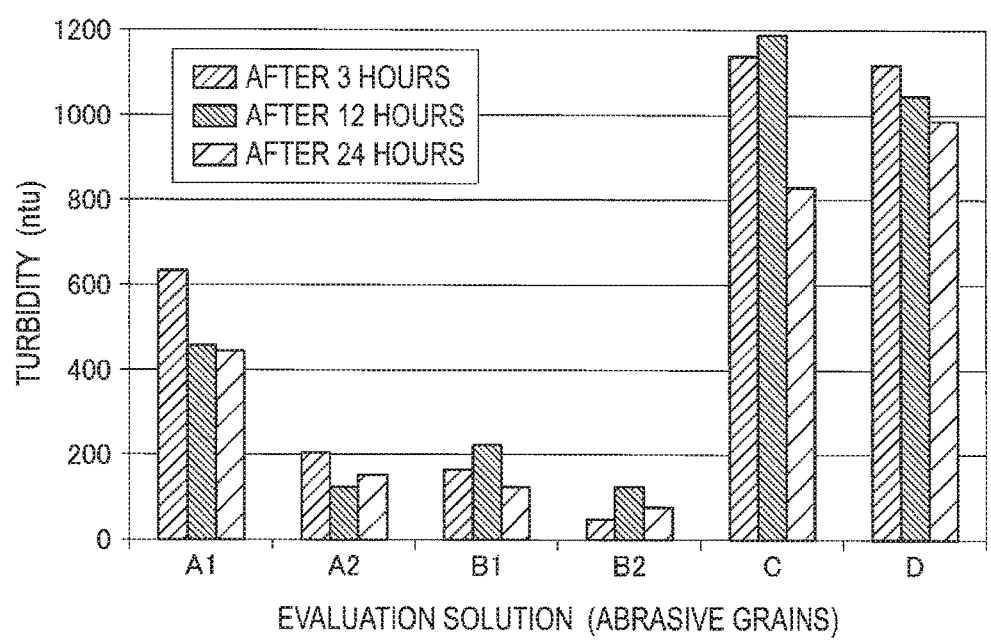
FIG. 4 is a graph showing a relationship between the stand-still time, the abrasive grains and the turbidity in Experiment 2 in Examples.

After preparing the same evaluation solutions A1, A2, B1, B2, C, D as those prepared in the Experiment 1 and the evaluation solutions were left still for 3, 12 and 24 hours at a normal temperature, the turbidities of the supernatants of the evaluation solutions were measured using the above turbidity meter. The results are shown in FIG. 4. The turbidity was also visually checked.

It should be noted that, when the stand-still time exceeds 24 hours, it becomes difficult to manage the receipt and stock of the abrasive grains during mass production. Accordingly, the maximum value of the stand-still time is set at 24 hours.

As shown in FIG. 4, though the measured values of the turbidity measured using the turbidity meter were lower in the evaluation solutions B1, B2 than those of the other evaluation solutions, the turbidity was larger than those of the other evaluation solutions in a visual check. Consequently, it was found that the measured value of the turbidity was not the same as the visual observation result irrespective of the length of the stand-still time.

In view of the above, it is understood that the turbidity of the supernatant cannot be reduced only by lengthening the stand-still time.

Experiment 3

In view of the results of the Experiment 2, it was checked whether or not the amount of the impurities could be appropriately estimated using the turbidity meter by diluting the supernatant of the evaluation solution even when much amount of impurities were present in the abrasive grains.

After the evaluation solution A1 identical with that in the Experiment 1 was prepared in three colorimetric tubes and was left still for 3 hours at a normal temperature, the supernatants in the respective colorimetric tubes were diluted twofold, fivefold and tenfold with pure water. The turbidities of the diluted supernatants were measured using the above turbidity meter. Similarly, the turbidities of the supernatants of the evaluation solutions A2, B1, B2, C, D diluted twofold, fivefold and tenfold with pure water were measured using the turbidity meter. The results are shown in FIG. 5.

Figure 5:
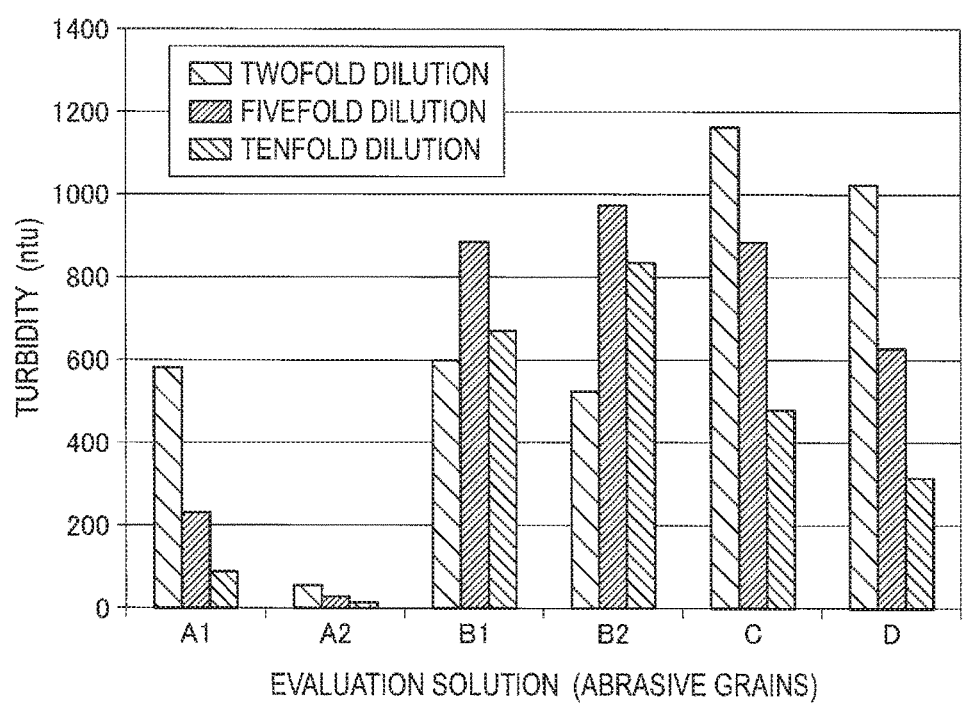
FIG. 5 is a graph showing a relationship between a dilution ratio of a supernatant, the abrasive grains and the turbidity in Experiment 3 in Examples.

As shown in FIG. 5, when the solutions were diluted twofold with pure water, the measured values of the supernatants of the evaluation solutions B1, B2 were lower than those of the supernatants of the evaluation solutions C, D. When the solutions were diluted fivefold with pure water, the measured value of the supernatant of the evaluation solutions B1 was substantially equal to that of the supernatant of the evaluation solution D. In either dilution ratios, the measured values of the supernatants was not the same as the visual observation result. In contrast, when the solutions were diluted tenfold with pure water, the measured values of the supernatants of the evaluation solutions B1, B2 were larger than those of the supernatants of the evaluation solutions A1, A2, C, D and the measured values of the supernatants were substantially the same as the visual observation results.

Figure 6:
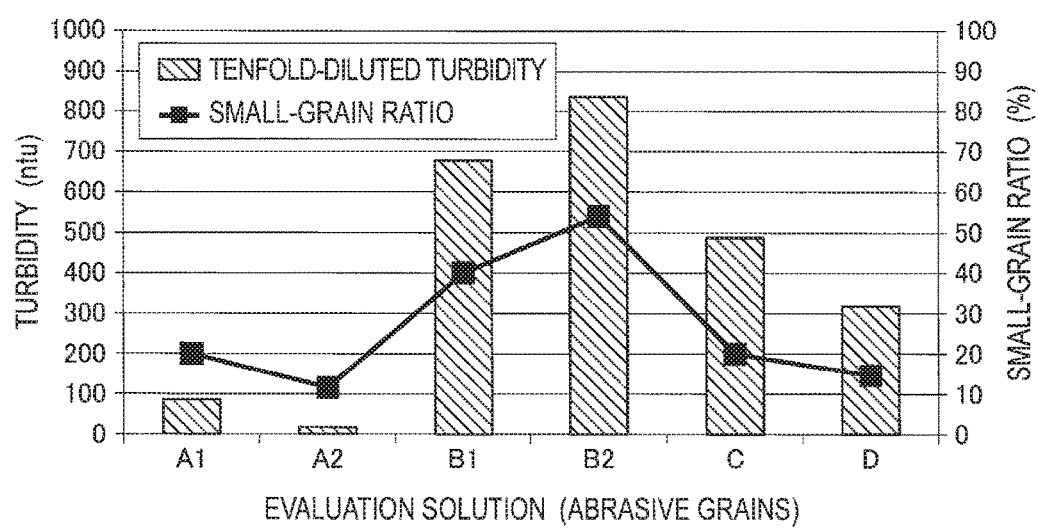
FIG. 6 is a graph showing a relationship between measured values of the turbidity of a tenfold diluted supernatant and a small-grain ratio of each of the abrasive grains in Experiment 3 in Examples.

Using a grain-size-distribution measuring machine (manufactured by Sysmex Corporation, Model No.: FPIA3000S), grain size distribution of each of the abrasive grains A1, A2, B1, B2, C, D was measured and a ratio of particles of 3 μm or less to the entirety of the abrasive grains was calculated as a small-grain ratio. It should be noted that, when the concentration in a target solution is large, a large number of agglomerated abrasive grains are produced. Accordingly, when the grain size distribution was measured, a mixture obtained by further diluting the evaluation solution used in the Experiment 1 fivefold with pure water was used. FIG. 6 shows a relationship between the measured values of the turbidity of the tenfold diluted supernatant and the small-grain ratio of each of the abrasive grains.

As shown in FIG. 6, though the measured value of the turbidity of the evaluation solution C was larger than that of the evaluation solution A1, the small-grain ratio of the abrasive grains A1 and the small-grain ratio of the abrasive grains C are substantially the same. Accordingly, it is understood that the measured value of the turbidity is not proportional to the small-grain ratio based on the measurement result of the grain-size-distribution measuring machine. On the other hand, it is understood that the measured value of the turbidity shown in FIG. 6 is substantially the same as the evaluation results of the visual check of each of the evaluation solutions.

In view of the above, it is understood that, even when much amount of the impurities are present in the abrasive grains, the turbidity of the supernatant can be appropriately measured using the turbidity meter by the tenfold dilution of the supernatant of the evaluation solution, and the amount of the impurities can be correctly estimated to based on the measurement results.

Study on Shaking Step

Experiment 4

The evaluation solution is manually prepared in the study of the dilution step, where the speed and length of time for shaking the colorimetric tube in order to mix the abrasive grains and the solvent may affect the measured value of the turbidity. Accordingly, a relationship between (i) the speed (number/min) and the number of times (one time=one reciprocatory motion) for shaking the colorimetric tube through a manual operation, and (ii) the measured value of the turbidity was examined.

Figure 7:
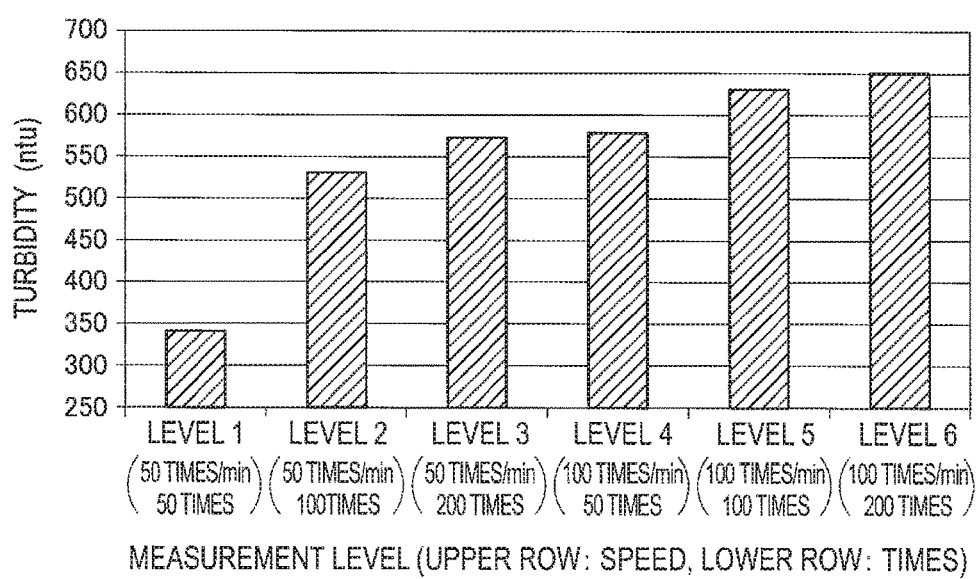
FIG. 7 is a graph showing a relationship between shaking conditions and the turbidity in Experiment 4 in Examples.

After preparing an evaluation solution using the abrasive grains B of the B company under the same conditions as those in the Experiment 1, the colorimetric tube was shaken under the conditions of levels 1 to 6 shown in FIG. 7. The shake width of the colorimetric tube through the manual operation is in a range from 100 mm to 150 mm. Subsequently, the colorimetric tube was left still for 3 hours to settle the polishing grains. Then, the supernatant was diluted tenfold with pure water and the turbidity of the diluted supernatant was measured using the turbidity meter. The results are shown in FIG. 7.

As shown in FIG. 7, as the shaking speed and the number of shaking increase, the measured value of the turbidity becomes large.

Based on the above, it is understood that the variation in the speed and time for shaking the colorimetric tube when the evaluation solution is prepared results in the variation in the measured value of the turbidity.

Experiment 5

Based on the results of the Experiment 4, it is believed that the use of shaker for preparing the evaluation solution can restrain the variation of the measured values of the turbidity. Accordingly, the most appropriate shaking condition using the shaker was examined.

Figure 8:
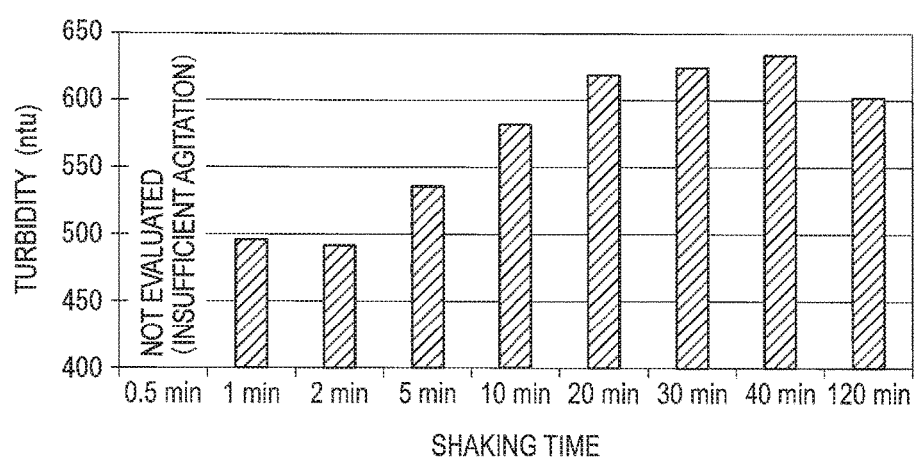
FIG. 8 is a graph showing a relationship between a shaking time and the turbidity in Experiment 5 in Examples.

After preparing the evaluation solution using the abrasive grains B in the same manner as the Experiment 4, the colorimetric tube was shaken for the shaking time periods shown in FIG. 8. A small reciprocation shaker NR-1 (specification: shaking speed of 20 to 200 times/min, shake width of 10 to 40 mm) manufactured by TAITEC CORPORATION was used as the shaker. The shake width and shaking speed of the colorimetric tube were respectively 40 mm and 200 times/min. Subsequently, the colorimetric tube was left still for 3 hours to settle the polishing grains. Then, the supernatant was diluted tenfold with pure water and the turbidity of the diluted supernatant was measured using the turbidity meter. The results are shown in FIG. 8.

As shown in FIG. 8, when the shaking time was less than 20 minutes, the measured value of the turbidity became larger as the shaking time became longer. However, when the shaking time exceeded 20 minutes, no noticeable change was seen in the measured value of the turbidity even when the shaking time got longer.

Based on the above, it is understood that the variation of the measured value of the turbidity can be restrained using the shaker under the conditions of the shake width of 40 mm, shaking speed of 200 times; min and shaking time of 20 minutes or more.

Experiment 6

It is understood that the variation of the measured value of the turbidity can be restrained using the shaker based on the results of the Experiment 5. However, for the convenience at a manufacturing site of the silicon wafer, it is preferable that the measured value of the turbidity is hardly affected even when the stand-still time after shaking the colorimetric tube is set at approximately 3 hours.

Accordingly, an influence of the stand-still time after shaking the colorimetric tube on the measured value of the turbidity was examined.

After preparing the evaluation solution using the abrasive grains B in the same manner as the Experiment 4, the colorimetric tube was shaken using the shaker used in the Experiment 5. The shake width, shaking speed and shaking time of the colorimetric tube were respectively 40 mm, 200 times/min and 20 minutes. Subsequently, the colorimetric tube was left still for the stand-still times shown in FIG. 9 to settle the polishing grains. Then, the supernatant was diluted tenfold with pure water and the turbidity of the diluted supernatant was measured using the turbidity meter. The results are shown in FIG. 9.

Figure 9:
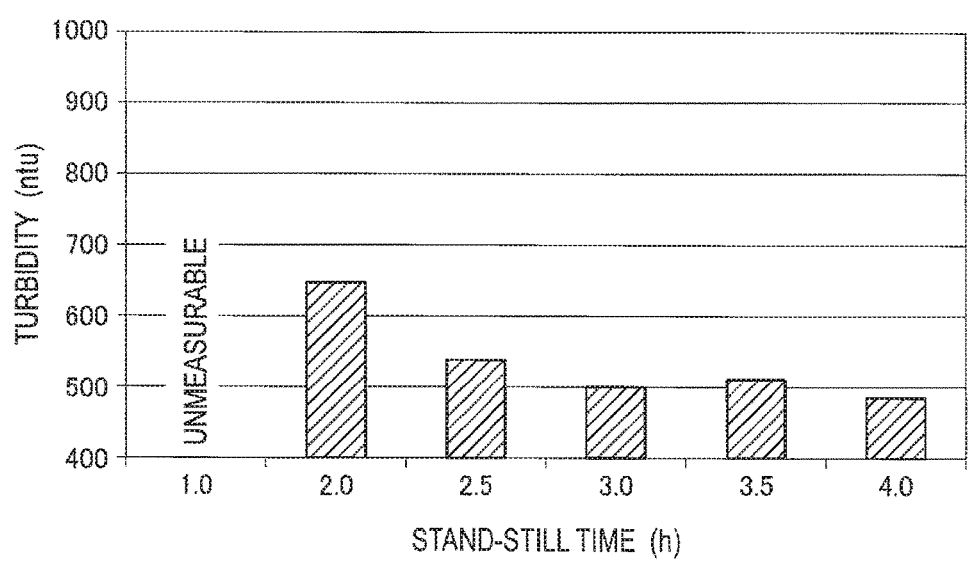
FIG. 9 is a graph showing a relationship between the stand-still time and the turbidity in Experiment 6 in Examples.

As shown in FIG. 9, when the stand-still time was less than 3 hours, the measured value of the turbidity became smaller as the stand-still time became longer. However, when the stand-still time was in a range from three to four hours, no noticeable change was seen in the measured value of the turbidity. It should be noted that the influence of the stand-still time exerted on the measured value of the turbidity when the stand-still time exceeds four hours is not known.

Based on the above, it is understood that the measured value of the turbidity is hardly affected when the colorimetric tube is shaken using the shaker under the conditions of shake width of 40 mm, shaking speed of 200 times/min and shaking time of 20 minutes or more and the subsequent stand-still time is in a range from three to four hours.

Effectiveness of Evaluation Method of Abrasive Grains

Next, effectiveness of the evaluation method of the abrasive grains of the exemplary embodiment will be described below.

Experiment 7

Comparatives

Abrasive grains E manufactured by E company and abrasive grains F manufactured by F company were prepared as the abrasive grains to be evaluated. The particle size of each of the abrasive grains was #2000.

Using the grain-size-distribution measuring machine used in the Experiment 3, grain size distribution of each of the abrasive grains E, F was measured and the small-grain ratio representing the ratio of particles of 3 μm or less was calculated. It should be noted that, when the grain size distribution was measured, a mixture obtained by further diluting a mixture of 30 gram of abrasive grains and 70 ml of pure water fivefold with pure water was used for the same reasons as those in Experiment 3. The measurement results of the grain size distribution are shown in FIG. 10 and the calculation results of the small-grain ratio are shown in FIG. 11.

Figure 10:
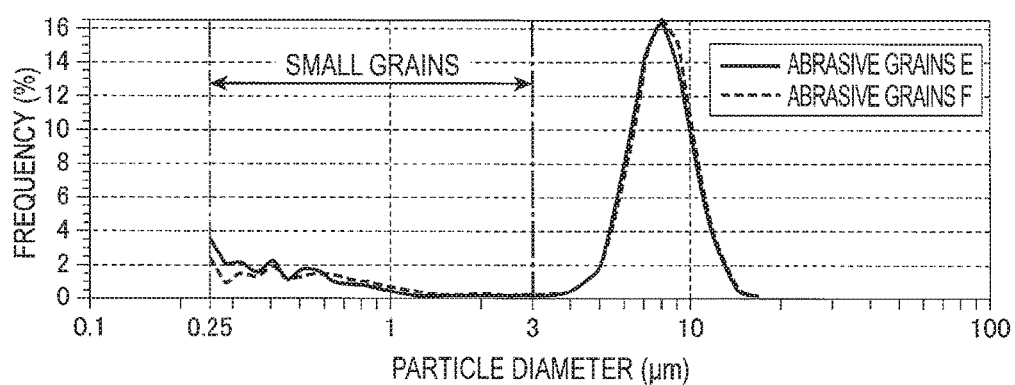
FIG. 10 is a graph showing a grain size distribution of abrasive grains in Comparative in Experiment 7 in Examples.
Figure 11:
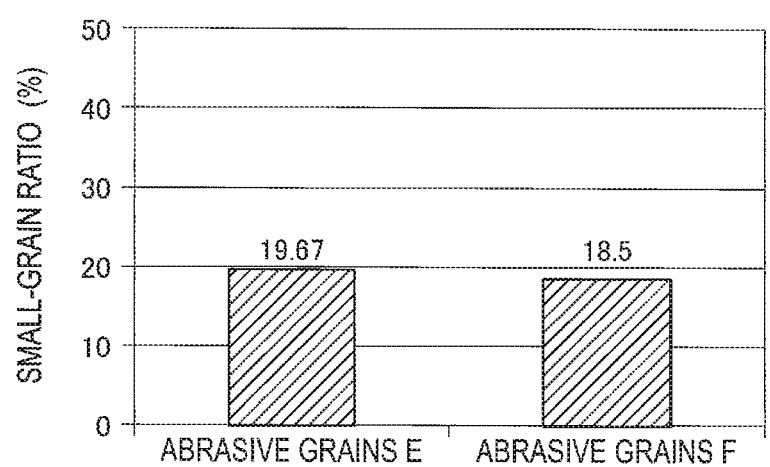
FIG. 11 is a graph showing a small-grain ratio of abrasive grains in Comparative in Experiment 7 in Examples.

As shown in FIGS. 10 and 11, no significant difference is observed between the abrasive grains E and abrasive grains F in terms both of the grain size distribution and the small-grain ratio.

Based on the above, it is understood that there is no significant difference in the measurement using the grain-size-distribution measuring machine in terms of the amount of the micro-particles (polishing grains+impurities (e.g. FC)) in the abrasive grains E, F.

Examples

The same abrasive grains E, F as those in the above Comparative were prepared. Then, the abrasive grains E, F were subjected to the processes of Step S1 to S6 according to the evaluation method of abrasive grains of the exemplary embodiment shown in FIG. 2.

In the evaluation solution preparation step (Step S1), 30 gram of the abrasive grains E was mixed with 70 ml of pure water through a manual operation of an operator to prepare an evaluation solution E. Similarly, an evaluation solution F was prepared by mixing 30 gram of abrasive grains F and 70 ml of pure water.

In the shaking step (Step S2), the shaker used in the Experiment 5 was used to shake colorimetric tubes respectively containing the evaluation solutions E, F under the conditions of the shake width of 40 mm, shaking speed of 200 times/min and shaking time of 20 min.

In the sedimentation step (Step S3), the colorimetric tubes after experiencing the shaking step were left still for 3 hours.

In the dilution step (Step S4), the supernatants of the evaluation solutions E, F having experienced the sedimentation step were diluted tenfold with pure water.

In the measurement step (Step S5), the turbidity meter used in the Experiment 1 was used to measure the turbidity of the supernatants of the evaluation solutions E, F having experienced the dilution step. In the estimation step (Step S6), based on the turbidity measurement results, the respective amounts of the impurities contained in the abrasive grains E, F were estimated.

Figure 12:
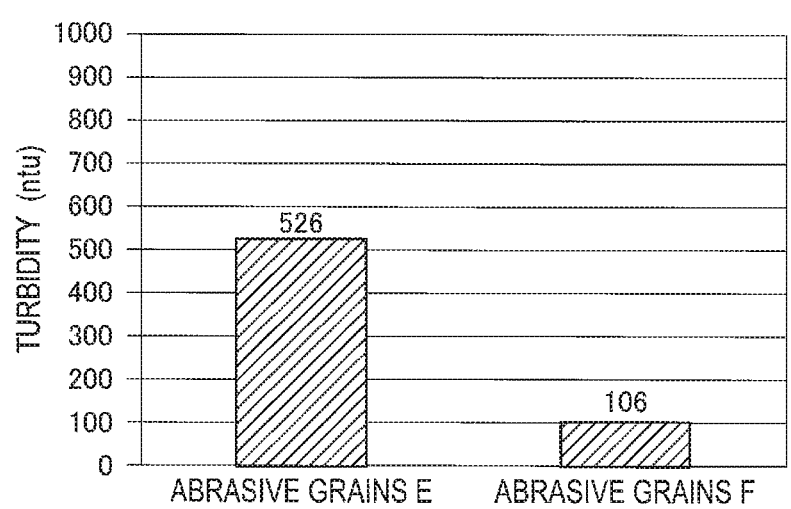
FIG. 12 is a graph showing the turbidity of the abrasive grains in an example in Experiment 7 in Examples.

The turbidity measurement results are shown in FIG. 12.

As shown in FIG. 2, the turbidity of the abrasive grains E is approximately five times as large as the turbidity of the abrasive grains F and a large difference is observable between the abrasive grains E, F.

In view of the above, it is estimated through the process according to the evaluation method for abrasive grains of the exemplary embodiment that the amount of the impurities contained in the abrasive grains E is approximately five times as much as the impurities contained in the abrasive grains F based on the measurement result of turbidity. It can also be estimated that the quality of the silicon wafer produced using the abrasive grains E is inferior to the quality of the silicon wafer produced using the abrasive grains F.

Experiment 8

Next, silicon wafers were produced using the abrasive grains E, F.

Specifically, slurry was prepared using the abrasive grains E taken from the same lot as the evaluated abrasive grains E and water soluble oil, and the slurry was used to cut an ingot to produce a silicon wafer of 300 mm diameter. Further, slurry was similarly prepared using the abrasive grains F and an ingot was cut using the slurry to produce a silicon wafer.

The quality of a cut surface of the produced silicon wafer was evaluated with reference to a thickness fluctuation. The results are shown in FIG. 13.

It should be noted that the thickness fluctuation refers to the number of sections of a thickness cross section divided into 10-mm sections in the cutting direction of the silicon wafer (Z direction in FIG. 1) whose PV value exceeds a thickness threshold, the PV value of the thickness being defined as [maximum thickness in the section]-[minimum thickness in the section] for each of the sections. The above thickness threshold was set at 1 µm, and the number of sections in the silicon wafer was 29 sections/wafer (in a 300 mm diameter silicon wafer, where 5-mm sections from the edges of the wafer was excluded from the evaluation). It should be noted that a flatness measuring machine SBW-330 manufactured by Kobelco Research Institute, Inc. was used as a thickness measurement machine.

Figure 13:
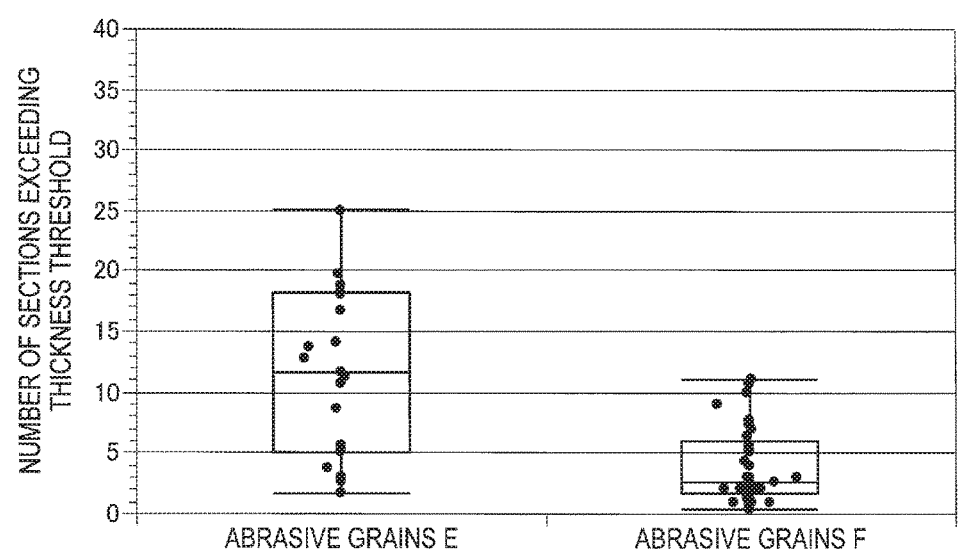
FIG. 13 is a graph showing a thickness fluctuation of a silicon wafer in Experiment 8 in Examples.

As shown in FIG. 13, it is confirmed that the quality of the silicon wafer produced using the abrasive grains E is inferior to the quality of the silicon wafer produced using the abrasive grains F. The above is the same as the result speculated based on the measurement results shown in FIG. 12.

Thus, it is understood that, by performing the processes according to the evaluation method of the abrasive grains of the exemplary embodiment, whether or not a high-quality silicon wafer can be obtained can be appropriately judged before the ingot T is cut using the abrasive grains taken from the same lot as the evaluated abrasive grains.

The invention claimed is:

1. An evaluation method of abrasive grains suitable for an ingot-cutting slurry, the evaluation method comprising:
   providing abrasive grains comprising polishing grains consisting of green silicon carbide, which contributes to cutting an ingot, and
   impurities consisting of a form of tree carbon, which do not contribute to cutting the ingot:
   preparing an evaluation solution by dissolving a test portion of the abrasive grains in a solvent;
   settling the polishing grains by leaving still a container containing the evaluation solution for a period of time sufficient to settle the green silicon carbide but to leave the impurities present in a supernatant of the evaluation solution;
   measuring a turbidity of the supernatant of the evaluation solution using a turbidity measurement device;
   determining that the abrasive grains are unusable if the turbidity of the supernatant exceeds a preset level; and
   determining that the abrasive grains is acceptable if the turbidity of the supernatant does not exceed a predetermined level.

2. The evaluation method of abrasive grains according to claim 1, wherein
   the solvent is water, pure water or ultra-pure water.

3. The evaluation method of abrasive grains according to claim 1, wherein
   the settling is performed after shaking the container containing the evaluation solution.

4. The evaluation method of abrasive grains according to claim 1, wherein
   the measuring is performed after diluting the supernatant.

5. A manufacturing method of a silicon wafer using a wire saw, the method comprising:
   evaluating one or a series of batches of abrasive grains used in the ingot-cutting slurry according to claim 1; and
   where a batch of abrasive grains is determined to be acceptable, preparing the ingot-cutting slurry using the batch of abrasive grains; and
   cutting an ingot using the wire saw and the ingot-cutting slurry to produce the silicon wafer.

* * * * *